(12) United States Patent
Kosecoff

(10) Patent No.: US 11,788,886 B2
(45) Date of Patent: Oct. 17, 2023

(54) WEARABLE DEVICE AND METHOD FOR MEASURING ULTRA-VIOLET LIGHT WITH VISIBLE LIGHT SENSOR

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 191 days.

(21) Appl. No.: 17/116,844

(22) Filed: Dec. 9, 2020

(65) Prior Publication Data

US 2022/0178744 A1  Jun. 9, 2022

(51) Int. Cl.
  *G01J 1/42* (2006.01)
  *G01J 1/58* (2006.01)
  *H04Q 9/00* (2006.01)
  *G16H 50/30* (2018.01)

(52) U.S. Cl.
  CPC ............... *G01J 1/58* (2013.01); *G01J 1/429* (2013.01); *G16H 50/30* (2018.01); *H04Q 9/00* (2013.01); *G01J 2001/4266* (2013.01); *H04Q 2209/40* (2013.01)

(58) Field of Classification Search
  CPC ...... G01J 1/58; G01J 1/429; G01J 2001/4266; G01J 1/0233; G01J 1/0219; G16H 50/30; H04Q 9/00; H04Q 2209/40; G08C 23/04; G08C 2201/93
  See application file for complete search history.

(56) References Cited

U.S. PATENT DOCUMENTS

| | | | |
|---|---|---|---|
| 4,065,672 A | 12/1977 | Harpster | |
| 6,140,651 A * | 10/2000 | Justus | G01T 3/06 |
| | | | 250/484.5 |
| 2002/0003619 A1 | 1/2002 | Ahlers et al. | |
| 2005/0235848 A1* | 10/2005 | Butland | G07D 7/128 |
| | | | 101/327 |
| 2009/0223635 A1* | 9/2009 | Lawless | G01N 21/94 |
| | | | 250/206 |

(Continued)

FOREIGN PATENT DOCUMENTS

JP  1-262425 A  10/1989
JP  H0621816 B2 * 10/1989

(Continued)

OTHER PUBLICATIONS

Translation of JP-H0621816 (Year: 1994).*

(Continued)

*Primary Examiner* — David P Porta
*Assistant Examiner* — Mamadou Faye
(74) *Attorney, Agent, or Firm* — Christensen O'Connor Johnson Kindness PLLC

(57) ABSTRACT

A wearable UV sensor includes a UV pass filter; a UV phosphor material; and a visible light sensing device, wherein the UV sensor is configured to receive light including visible light and UV light, wherein the UV pass filter directs the UV light to the UV phosphor material and the UV phosphor material fluoresces visible light in proportion to the UV light from the UV pass filter, and the visible light sensing device measures the visible light fluorescing from the UV phosphor material to determine the amount of the UV light entering the sensor, which correlates to the UV exposure of a subject wearing the UV sensor.

17 Claims, 7 Drawing Sheets

(56) References Cited

U.S. PATENT DOCUMENTS

| | | |
|---|---|---|
| 2015/0177055 A1 | 6/2015 | Lian et al. |
| 2016/0142660 A1* | 5/2016 | Shen ................. H01L 27/14621 438/69 |
| 2019/0204146 A1* | 7/2019 | Wei ....................... G01J 1/0219 |

FOREIGN PATENT DOCUMENTS

| | | |
|---|---|---|
| WO | 2013/034288 A1 | 3/2013 |
| WO | 2015/006656 A2 | 1/2015 |

OTHER PUBLICATIONS

Service, Robert F. "New material converts invisible, infrared energy into visible light", ScienceMag.Org, Jun. 9, 2016, https://www.sciencemag.org/news/2016/06/new-material-converts-invisible-infrared-energy-visible-light.

French Preliminary Search Report dated Apr. 1, 2022, issued in corresponding Application No. FR2108083, filed Jul. 26, 2021, 8 pages.

* cited by examiner

WEARABLE DEVICE AND METHOD FOR MEASURING ULTRA-VIOLET LIGHT WITH VISIBLE LIGHT SENSOR

SUMMARY

In one embodiment, a UV sensor comprises a UV pass filter; a UV phosphor material; and a visible light sensing device, wherein the UV sensor is configured to receive light including visible light and UV light, wherein the UV pass filter directs the UV light to the UV phosphor material and the UV phosphor material fluoresces visible light in proportion to the UV light from the UV pass filter, and the visible light sensing device measures the visible light fluorescing from the UV phosphor material to determine an amount of the UV light entering the UV sensor.

In one embodiment, the UV pass filter transmits the UV light and blocks the visible light and infrared light.

In one embodiment, the UV sensor comprises circuitry to wirelessly transfer data to a client device.

In one embodiment, the UV sensor comprises a memory configured to store data generated by the visible light sensing device.

In one embodiment, the UV sensor comprises a photodiode to measure the visible light fluorescence.

In one embodiment, a combination of the UV sensor and a client device is described, wherein the UV sensor is configured to communicate data to the client device.

In one embodiment, the client device is a smart phone.

In one embodiment, the client device is configured to display the UV intensity.

In one embodiment, the client device is configured to display a cumulative UV exposure.

In one embodiment, the client device is configured to process the data from the UV sensor on a client device processor.

In one embodiment, the client device is configured to transfer the data from the UV sensor to a server for processing the data.

In one embodiment, a method of measuring UV exposure of a subject comprises wearing a UV sensor by a subject; filtering UV light entering the UV sensor from visible light entering the UV sensor; causing fluorescence of visible light from the filtered UV light that is in proportion to the filtered UV light; measuring the fluorescent visible light; and calculating UV light entering the sensor from the amount of fluorescent visible light to obtain an estimate of UV exposure of a subject.

In one embodiment, the method further comprises transferring data from the UV sensor to a client device, wherein the client device calculates the amount of UV light entering the sensor.

In one embodiment, the client device displays the UV exposure of the subject on a display device of the client device.

In one embodiment, a wearable sensor comprises an ultraviolet verification unit coupled to one or more optical sensors and an ultraviolet phosphor element configured to fluoresce in the visible light spectrum responsive to an interrogation by an ultraviolet stimulus, wherein the wearable sensor includes at least one ultraviolet pass filter assembly configured to block the visible portion of an impinging optical radiation stimulus, pass the ultraviolet portion of the impinging optical radiation stimulus onto the ultraviolet phosphor element; and wherein the ultraviolet verification unit includes processing circuitry configured to generate one or more instances of an ultraviolet exposure level based on a portion of a detected fluorescent response of the ultraviolet phosphor element that ranges from 400 nanometers to 700 nanometers.

In one embodiment, the ultraviolet verification unit includes a graphical user interface configured to generate the one or more instances of the ultraviolet exposure level based on the portion of a detected fluorescent response of the ultraviolet phosphor element that ranges from 400 nanometers to 700 nanometers.

In one embodiment, the ultraviolet verification unit includes a graphical user interface configured to generate the one or more instances of the ultraviolet exposure duration, an ultraviolet exposure intensity, an ultraviolet exposure severity, and a user-specific lifetime ultraviolet exposure status based on the portion of a detected fluorescent response of the ultraviolet phosphor element that ranges from 400 nanometers to 700 nanometers.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Excessive ultraviolet (UV) radiation has acute and chronic effects on the skin, eyes, and immune system. Personalized monitoring of UV radiation is thus paramount to measure the extent of personal sun exposure, which could vary with environment, lifestyle, and sunscreen use.

UV radiation is also necessary for production of vitamin D and beneficial for human health, but over-exposure to UV has many associated risk factors, including skin cancer and photo-aging, even long after UV exposure ends. Continuous sunscreen protection and monitoring of personal UV exposures is therefore useful for better skin protection and prevention of skin cancer.

Currently, there are various UV sensors that can be worn on a person for measuring UV exposure. However, current sensors for measuring UV light intensity require specialized, expensive photodiodes.

In this disclosure, a UV sensor and method are disclosed for measuring UV intensity by measuring visible light intensity using common, inexpensive ambient light sensors or photodiodes. In accordance with this disclosure, in order to reduce material cost of a UV sensor product, an ambient light sensor can be used in conjunction with an optical medium that converts UV light into visible light. The visible light is emitted in proportion to the UV light. Therefore, by measuring the visible light emitted by the optical material, the intensity of UV can be calculated.

The optical medium, such as a UV phosphor, is placed above a visible-spectrum ambient light sensor. A UV-passing filter material is placed above this optical medium. Visible and UV light from the outside environment enter the UV-pass filter and only UV light exits. The UV light then passes or strikes the UV phosphor which is caused to fluoresce or give off light in the visible spectrum. The UV light may exit in the same direction(s) it entered. Then, this visible light fluorescence is measured by a visible-spectrum light sensor, such as a photodiode. The output of the visible spectrum light sensing element is proportional to the amount of UV light in the outside environmental. To compensate for losses in the UV-pass filter and conversion of UV to visible light, correction values can be applied to compensate for efficiency losses of the UV-pass filter and the UV phosphor material. The correction values will depend on the specific UV-pass filter and phosphor material used in the sensor.

Figure 1:
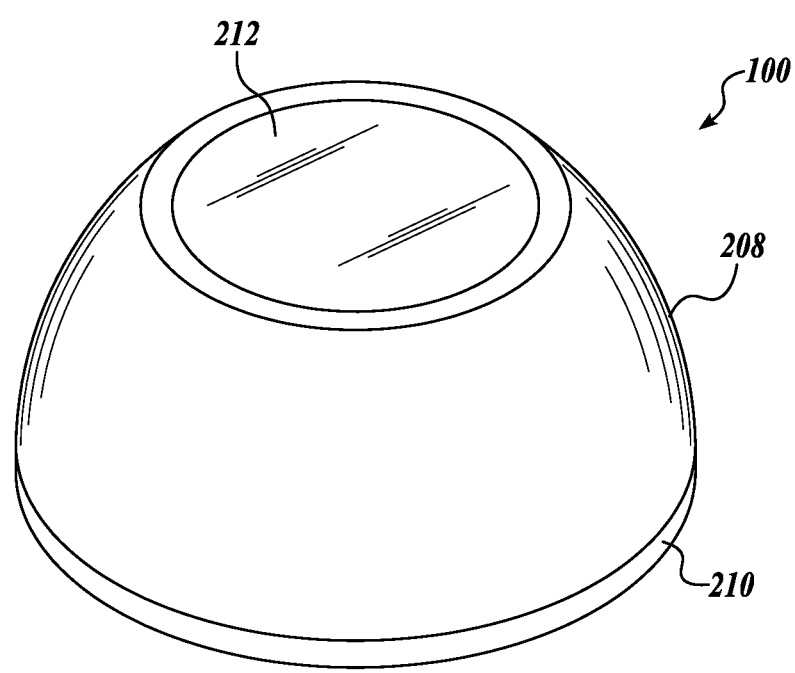
FIG. 1 is a diagrammatical illustration of a UV sensor.

FIG. 1 illustrates a UV sensor 100 according to one embodiment. The UV sensor 100 can be provided with a clip so as to enable the sensor to be worn on a person or clothing. In one embodiment, a miniaturized sensor 100 can be made sufficiently small to enable gluing to a fingernail. In one embodiment, the aim of UV sensor 100 is to measure UV exposure of the person wearing the sensor 100. In one embodiment, the UV sensor 100 can connect wirelessly to a smart phone application to display accumulated UV exposure over time, and provide functionality useful to the subject 102 wearing the UV sensor 100. Smart phones are now a commonplace device carried by many, therefore, the UV sensor 100 can be made to communicate with the smart phone to take advantage of the functions available on a smart phone, such as higher processing power, display, and user interface. In one embodiment, the sensor 100 can incorporate a UV verification unit into the sensor housing to perform similar functions of the smart phone.

Figure 2:
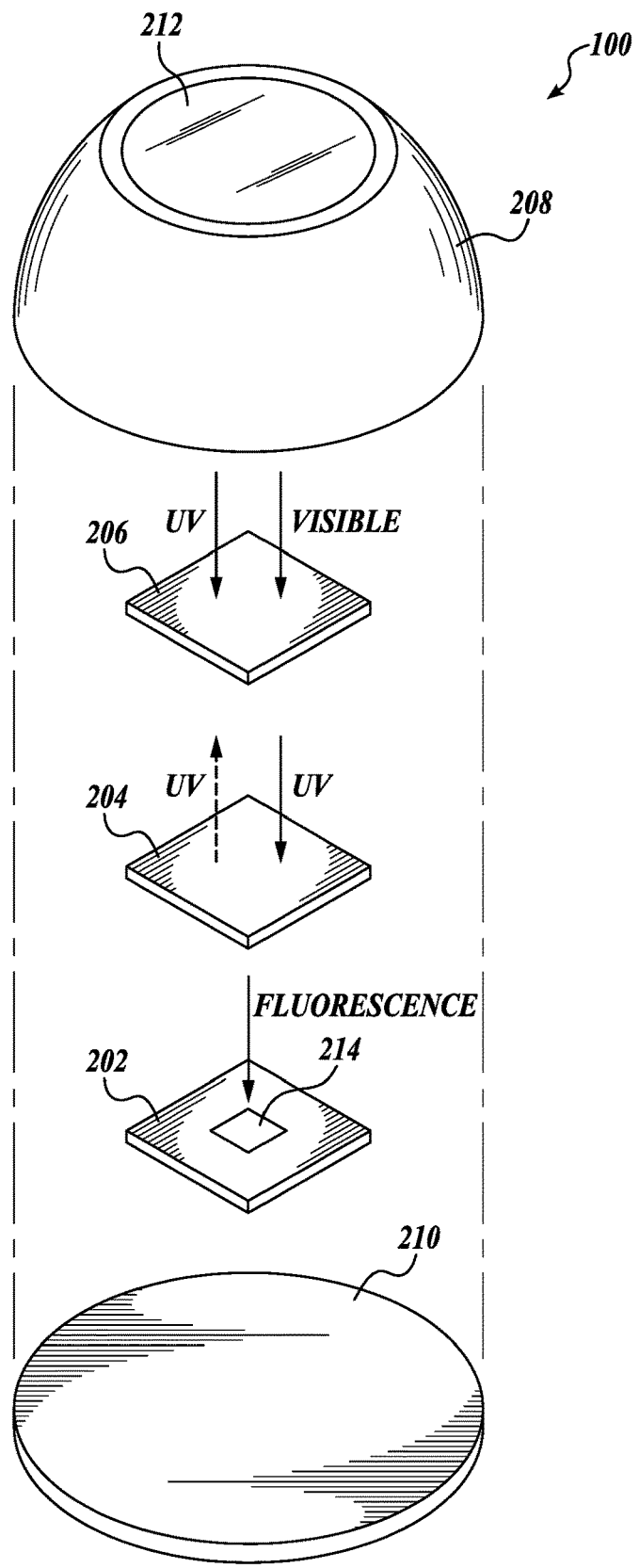
FIG. 2 is a diagrammatical illustration of an exploded view of the UV sensor of FIG. 1.

Referring to FIG. 2, a basic illustration of the sensor 100 shows the major components. Other components are not shown to avoid obscuring one or more aspects.

In one embodiment, the sensor 100 includes a base 210. The base 210 serves as an attachment point to any clip or other device to affix the sensor 100 to the person or clothing. In one embodiment, the sensor 100 includes a visible light sensing device 202, a UV phosphor material 204, and a UV-pass filter 206.

In one embodiment, ambient light (e.g. sunlight) enters the sensor 100 through a lens 212 fitted on a housing 208 that connects to the base 210. The lens 212 can be any optical medium that allows visible and UV light transmission. The ambient light which includes the visible and UV light passes through the lens 212 and enters the UV-pass filter 206. The UV-pass filter 206 can be in a direct path of the ambient light or the ambient light can be reflected to the UV-pass filter 206.

The UV-pass filter 206 is any material or combination of materials that allows the passage or transmission of electromagnetic energy in the UV range, but, blocks visible light. UV energy is defined to have a wavelength in the range of about 10 nm to 400 nm. UV can further be divided into subtypes including UVC, UVB, and UVA. Exposure to UVA and UVB are considered important for a person's health and well-being. UVC generally does not penetrate the earth's atmosphere. While some exposure to UVA and UVB can be beneficial because it leads to the production of vitamin D, overexposure to UVA and UVB or both can lead to harmful effects, such as sun burn, premature aging, and skin cancer.

In one embodiment, UVB is defined to have a wavelength of about 280 nm to about 315 nm. In one embodiment, UVA is defined to have a wavelength of about 315 nm to about 400 nm. The UV-pass filter 206 can be chosen to have a narrow or broad wavelength range. In one embodiment, the UV-pass filter 206 is a UVA-pass filter. In one embodiment, the UV-pass filter 206 is a UVB-pass filter. In one embodiment, the UV-pass filter 206 is a combined UVA- and UVB-pass filter. In one embodiment, the UV-pass filter 206 is a single filter which has a predetermined transmissivity range. In one embodiment, the UV-pass filter 206 can be interchangeable with other UV-pass filters of a broader or narrower transmissivity range in order to allow selection of UV in a specific wavelength. In one embodiment, the UV-pass filter 206 is an assembly of a plurality of individual filters which may allow to select a transmissivity of UVA or UVB or both UVA and UVB or even of more discrete wavelength ranges.

In one embodiment, the UV-pass filter 206 works by transmissivity of UV and blocking or absorbing of visible light. In one embodiment, the UV-pass filter 206 is constructed of materials that allow the transmissivity of the selected UV wavelength, while blocking out the visible light. The UV-pass filter 206 may include a plurality of filters in series, where each subsequent filter allows transmissivity of the desired wavelength while blocking energy outside of the desired wavelength. This can lead to a UV-pass filter passing a UV bandwidth having sharp edges, but, reduced transmissivity. In one embodiment, the UV-pass filter can have a high transmissivity of UV, but, can allow greater amount of visible light and infrared to also pass. It is appreciated that a UV-pass filter may not be 100% efficient in transmissivity of all UV light and 100% efficient in blocking all visible light and infrared light. In one embodiment, the UV-pass filter may allow some visible light and infrared light to pass through the UV-pass filter 206.

In one embodiment, the UV-pass filter 206 works by reflectance of UV. In one embodiment, the UV-pass filter is constructed of materials that allow the reflectance of the selected UV wavelength, while absorbing the visible light. The UV-pass filter 206 may include a plurality of reflective filters where each subsequent reflective filter reflects energy of the desired wavelength while absorbing or blocking energy outside of the desired wavelength.

In either case, the UV energy from the UV-pass filter 206 is directed to enter the UV phosphor material 206 either through a direct path or through one or more reflective devices.

The UV phosphor material 204 is a material that absorbs UV light and emits visible light or UV-induced visible fluorescence. The wavelength of the emitted visible light will depend on the specific UV phosphor material used. There are many materials that can fluoresce visible light by absorbing UV. Many UV phosphor materials fluoresce not along the entire visible light spectrum, but, only in a narrower range or a specific color, such as green, yellow, red, blue, etc.

UV phosphor materials 204 include ceramics, glass, borosilicate glass, crystal and lead glass, soda-lime glass. Some UV phosphor materials 204 may include a non-fluorescing substrate which is coated with a fluorescent coating. Some UV phosphor materials 204 can absorb UV and fluoresce visible light on the opposite side of the material. Suitable fluorescent coatings include waxes, such as beeswax, paraffin wax, and carnauba wax. Other UV phosphor materials may include, but are not limited to, cellulose, cellulose acetate, cellulose nitrate, copal, dextrin, epoxy adhesives, gum Arabic, LAROPAL 80 (ketone resin N), linseed oil, mastic, MOWILITH 50 (poly vinyl acetate), some varnishes and lacquers, dyes and pigments, cadmium red, cinnabar, eosin, red ochre, red lead, cadmium orange, cadmium yellow, nickel titanate, zinc yellow, chromium oxide, cobalt green, copper aceto-arsenite, phthalocyanine green, azurite, cobalt blue, phthalocyanine blue, cobalt violet, calcium carbonate, lithopone, titanium dioxide.

In one embodiment, the UV phosphor material 204 includes the fluorescent component as a powder which is mixed with an epoxy to provide a solid material. In one embodiment, the UV phosphor material can be coated onto a solid substrate. In one embodiment, the aim of the UV phosphor material 204 is to fluoresce visible light which is measured by the visible light sensing device 202.

In one embodiment, the visible light sensing device 202 is a solid state device that converts visible light into an electrical current. Solid state visible light sensors based on metal-oxide-semiconductor technology allow for a small, reliable, and inexpensive visible light sensor 202. In one embodiment, the visible light sensing device 202 includes a photodiode 214. The photodiode 214 can use any commonly available technology, such as charged-coupled device (CCD) and active-pixel sensor (CMOS) technologies or variations thereof.

In one embodiment, the visible light sensing device 202 is for measuring electromagnetic energy in the visible light spectrum. In one embodiment, the visible light spectrum is defined as electromagnetic energy which can be perceived by the human eye. In one embodiment, the visible light spectrum is defined as having a wavelength in the range of about 400 nm to about 740 nm. While the visible light sensing device 202 measures electromagnetic energy in the range of 400 nm to 740 nm, the visible light sensing device 202 can be made to sense a narrower range anywhere between 400 nm to 740 nm. For example, the visible light sensing device 202 is configured to detect visible light in the visible light wavelength emitted by the UV phosphor material 204, which may be limited to a particular color.

In one embodiment, the light sensing device 202 includes the photodiode 214 packaged into a chip including other circuits. These circuits can control the operation of the sensor 100, and may include a microprocessor, a memory module, a communications module, a power supply, and an antenna.

In one embodiment, the sensor 100 contains circuitry that will induce an electronic current proportional to visible light fluorescence entering the photodiode 214. The voltage is read each time as the subject 102 scans the sensor 100 and an application ("app") running on a client device 300 converts the voltage to UV measurement based on predetermined correlations and efficiencies. In one embodiment, the visible light sensing device 202 will induce electronic current proportional to the visible light fluorescence being emitted by the UV-phosphor material 206, which in turn is in proportion to the amount of UV energy entering the sensor 100. Then, the actual amount of UV energy entering the sensor 100 can be estimated by applying correction factors that consider the efficiency of the lens 212, the UV-pass filter 206, and the UV phosphor material 204 based on the measured amount of visible light fluorescence. Accordingly, the sensor 100 uses a visible light sensing device 202 to measure UV intensity to which a person is exposed.

Although FIG. 2 shows a generally linear path of ambient light entering the sensor 100 through the lens 212, then impinging the UV-pass filter 206 in a linear path, then the UV light impinging the UV phosphor material 204 in a linear path, then the fluorescent visible light impinging the photodiode 214 in a linear path, the components can be placed in different locations by the use of reflective surfaces. In one embodiment, for example, the phosphor material can be placed so as to receive light or fluoresce light indirectly. In this way, incoming light is directed into areas that are more desirable for placing the sensing componentry in the event that placing the sensing componentry directly underneath the sensor aperture is not ideal.

In one embodiment, the sensor 100 is for measuring the intensity of UVA, the UV-pass filter 206 is a UVA pass filter, and the app applies an algorithm for calculating UVB. The corresponding UVB exposure is calculated using a pre-computed lookup table that gives the conversion factor as function of the column amount of ozone in the atmosphere and solar zenith angle (SZA). SZA is determined based on GPS location and time. The subject latitude, longitude, and time are also used to extract the forecast ozone amount from satellite-measurements.

The UVA and UVB doses calculated by the app represents the amount of UV exposure that a subject 102 was exposed to during a period between two consecutive scans. The subject 102 can follow their UV exposure over time and determine their personal UV dose and whether such does is within a safe risk level.

In one embodiment, the sensor 100 uses circuitry to convert the UV intensity into an amount of UV exposure which can be stored as a cumulative UV exposure over time. In one embodiment, the sensor 100 is designed with NFC, RFID, and antenna, for a subject 102 to obtain the data wirelessly via the smart phone app. The smart phone app can be used to track a person's cumulative UV dosage, with predictive algorithms to monitor Vitamin D level, UV aging, and sun safety, for example.

Figure 3:
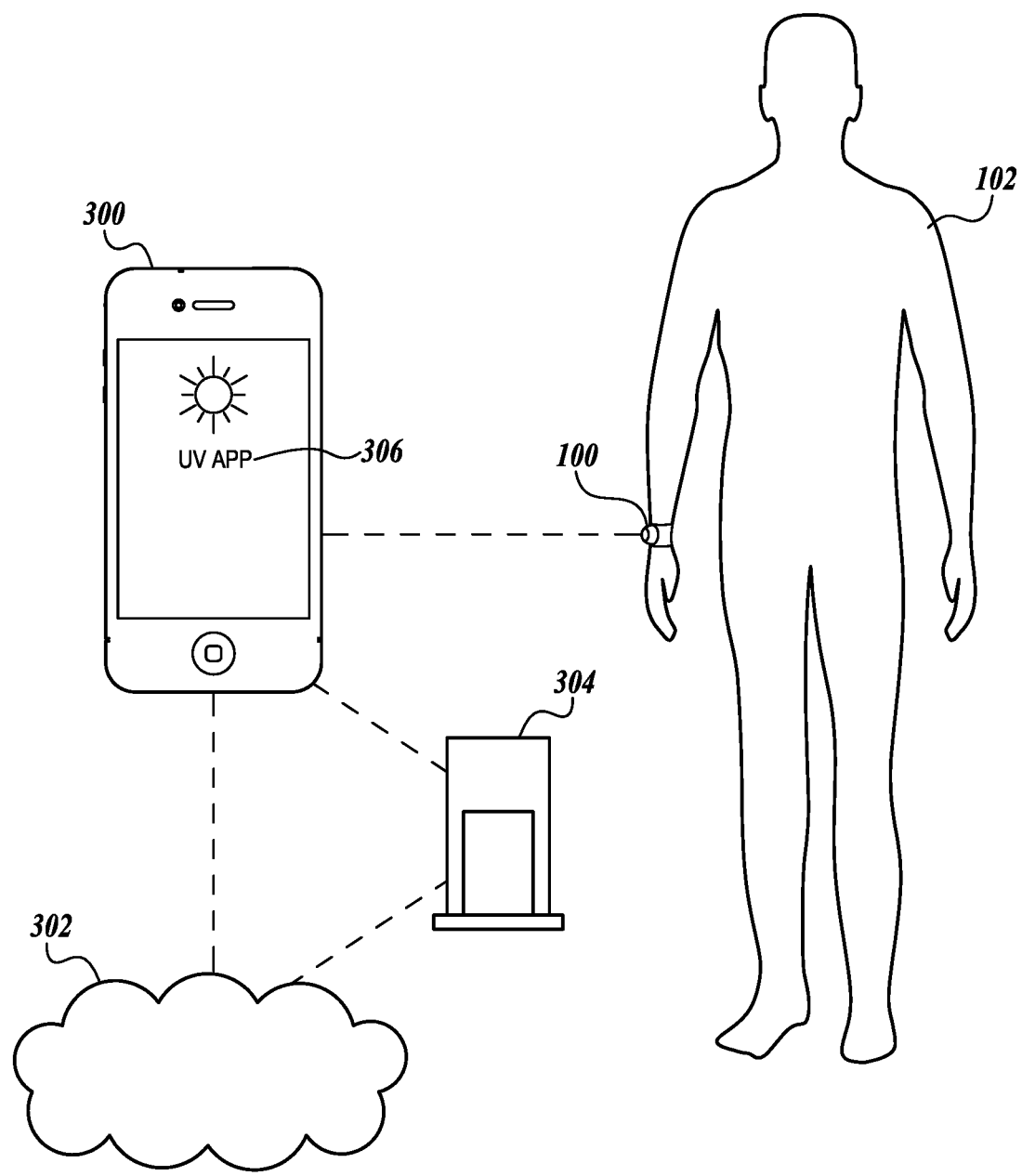
FIG. 3 is a diagrammatical illustration of a system for measuring UV exposure of a subject with the wearable UV sensor of FIG. 1.

FIG. 3 illustrates the sensor 100 may connect to a client device 300, such as a smart phone in one embodiment. The client device can also be a computer, tablet, or personal digital assistant. In one embodiment, the client device 300 is further configured to connect to a cloud computing environment which is connected to data analytics servers 304 through the Internet 302 for determining personalized UV doses for the subject 102 based on information provided by the client device 300 and sensor 100.

An application 306 on the client device 300 may use the UV measurement from the UV sensor 100 along with other factors, such as skin phototype, personal preferences, personal data, location, user IDs, and the environment (outside temperature, humidity, and pollution level) to further recommend a personal skin care regimen. The smart phone (client device) 300 can include circuitry and hardware as is known in the art. The smart phone 300 may include a CPU, an I/O interface, and a network controller such as BCM43342 Wi-Fi, Frequency Modulation, and Bluetooth combo chip from Broadcom, for interfacing with a network. The hardware can be designed for reduced size. For example, the CPU may be an APL0778 from Apple Inc., or may be other processor types that would be recognized by one of ordinary skill in the art.

Alternatively, the CPU may be implemented on an FPGA, ASIC, PLD or using discrete logic circuits, as one of ordinary skill in the art would recognize. Further, the CPU may be implemented as multiple processors cooperatively working in parallel (such as a cloud computing environment) to perform the instructions of the inventive processes described above.

In one embodiment, the personal daily safe UV doses are calculated based on the skin phototype and minimal erythema dose (MED). The skin phototype is determined by a questionnaire completed by the subject 102 when the subject 102 first opens the app 306. The maximal daily safe UV dose is set to about 0.8 MED in one example. The rate of change of the UV exposure throughout the day is calculated for every scan for the time between the current and previous scan. In addition, the daily, weekly, monthly, and yearly UV doses of the subject 102 can be calculated and displayed by the client device.

In one embodiment, the sensor 100 is connected to the cloud server 304. The data is uploading to the server 304 whenever a data network is available. The data can be analyzed on the client device 300 and on the server 304 while the results are available for subjects via the smart phone application. Subjects can access their data on the cloud server to examine their UV exposure patterns over time at different locations.

In one embodiment, the cloud server 304 includes one or more computing devices that each include one or more processors, non-transitory computer-readable media, and network communication interfaces that are collectively configured to provide the illustrated components. In one embodiment, the one or more computing devices that make up the cloud server 304 may be rack-mount computing devices, desktop computing devices, or computing devices of a cloud computing service.

In one embodiment, the could server 304 includes a "data store." Data store can refer to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally or over a network instead of a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores.

Data analysis may be performed by an "engine." "Engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

The client device 300 executes the app 306 using the sensor 100. The sensor 100 detects UV exposure as previously described and transmits the data to the client device 300. In one example, the sensor 100 transmits data multiple times at regular intervals (for example, every two hours) throughout the day. The client device 300 may provide an indication of the subject risk level in percentage form, along with a category label such as "low", "moderate," or "high." Additionally, other pieces of information may be displayed, such as location, current humidity, UV index, current temperature, pollen level, and air quality. A graph may also be displayed that tracks the UV exposure level over time for the day, and it may include further information taken from a subject's schedule (such as "afternoon run"). The display may also show a message based on the risk level, such as a congratulatory message ("well done") or a caution message ("Caution: your UV exposure increased 39% in the past hour"). There may be a display that shows both UVA and UVB exposure. The device display may be based on a daily display, a weekly display, or a monthly display.

In one embodiment, the sensor 100 is in communication with the client device 300 with a wireless signal. In an embodiment, the client device 300 is configured to operate the software application 306 as a set of engines to receive and send communications to and from the sensor 100. In an example, the application 306 tracks the UV sensor's UV measurements in real time.

The wireless signal can be any appropriate signal such as an electromagnetic signal including WIFI, Bluetooth, near-field, or any other signal such as optical, and acoustic. The client device 300 may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

FIG. 3 is an example of a system that includes at least the sensor 100 and the client device 300. Optionally, the system may further include one or more servers 304 which are implemented as part of a cloud-computing environment and in communication with the system through the Internet 302. The one or more external servers 304 can store subject data, products such as skincare products, skincare accessories, protocols and routines, tutorials, as well as other third party services according to an example.

In one embodiment, the user interface on the client device 300 can display tutorials on how to use skincare products or accessories. The user interface can create and download protocols for a regimen or routine. The user interface can coach, track usage and compare the tracked usage to the protocol, the regimen, and the routine. The user interface can calculate a score based on the tracked usage. The user interface can store the scores and the tracked usage of any appliances in the memory of the client device, or it can be uploaded to the server or servers 304. The user interface can be used to make a purchase of any products related to skincare or UV protection. For instance, the client device 300 can output recommendations on particular skincare products or compositions to be used, and which step in the process they are to be used, based on the desired results inputted by the subject 102.

In one embodiment, the client device 300 may collect information regarding a subject's desired results. The client device 300 may store search results locally or may connect to an external system or server to access the database or search results.

After the subject 102 finds a desired skincare result, the subject 102 may access tutorials for achieving the results. The tutorials may be in text form, still image form, video form, or audio-only form.

The client device 300 is configured to upload data regarding the subject 102 to an external system or server (such as a cloud-based system). Such data may include the subject profile, amount of use of skincare products or accessories, or performance results when using the skincare products or accessories. The client device 300 can also provide an option to keep the subject data anonymous.

Figure 4:
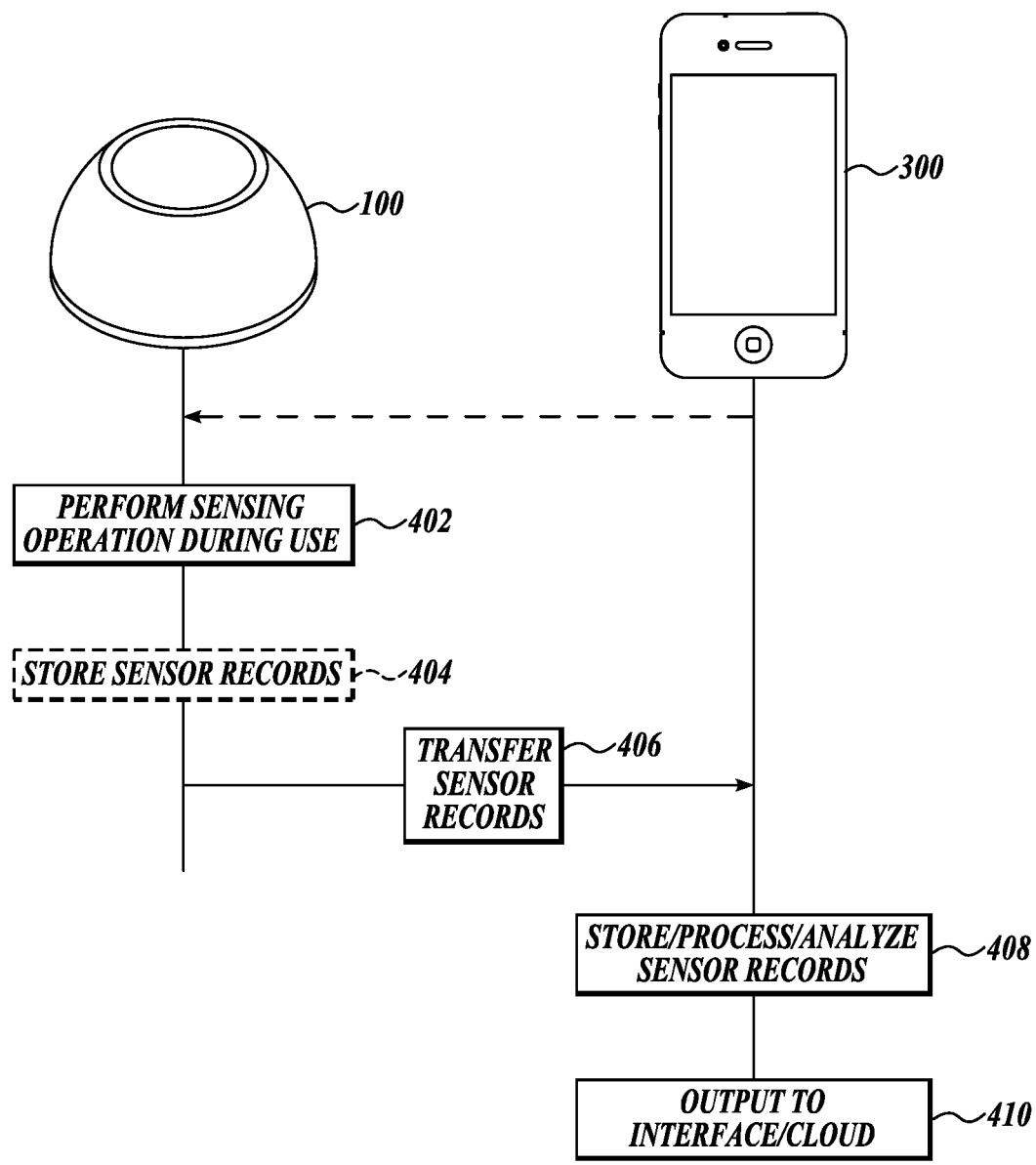
FIG. 4 is a diagrammatical illustration of a process for data transfer between the UV sensor of FIG. 1 and a client device.

FIG. 4 shows a general process performed among the sensor 100 and the client device 300. Communication pairing is performed between the sensor 100 and client device 300 when the two devices are within an acceptable wireless communication range of each other. Such pairing will depend on the type of communication protocol being used and such protocols are well understood in the art. The sensor 100 performs any of a number of sensing operations in step 402 for taking UV measurements as was described above. The sensor 100 records obtained by the sensing operations may be optionally stored in a local memory (e.g. by an RFID) in step 404 and/or immediately communicated to the client device 300 in step 406.

The client device 300 stores the sensed data received from the sensor 100 and performs processing and analyzing of the sensed data in step 408. Then, in step 410 the client device 300 may output the results on the display of the client device 300, and/or the client device 300 may output such results or other data to a cloud server 304, such as cloud server 304 shown in FIG. 3.

Figure 5:
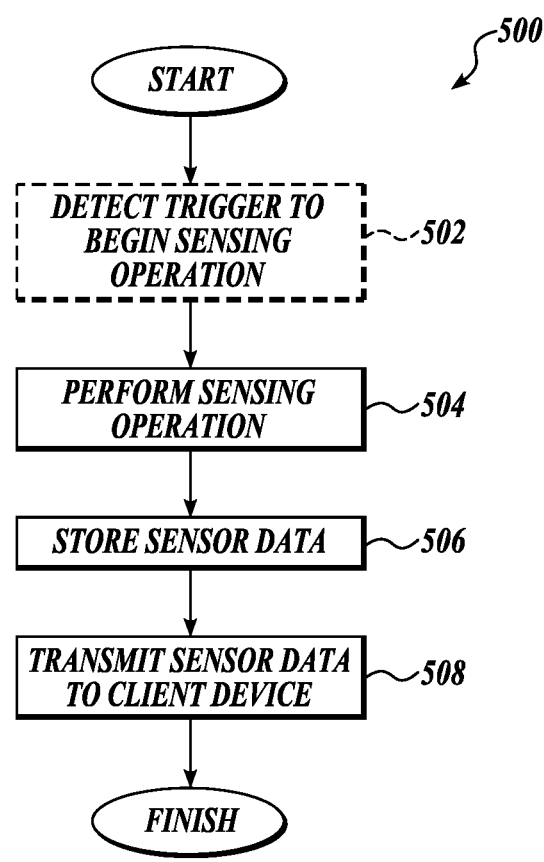
FIG. 5 is a flow diagram of a method performed by the UV sensor of FIG. 1.

FIG. 5 shows an algorithm that may be performed by the sensor 100 according to an embodiment. In step 502, the sensor 100 detects a trigger to begin sensing operation. This trigger may be automatic activation based on any exposure to the sun. The trigger may also be received from the client device itself. For instance, if communication pairing has been established between the sensor 100 and the client device 300, the client device 300 may transmit a signal to the sensor 100 to begin the sensing operation.

The sensing operation(s) is/are performed at step 504 by the sensor 100. In step 504, the sensor data obtained from the sensing operations are optionally stored in the memory of the sensor 100 as they are obtained. In step 508, the sensor data is transmitted to the client device 300. Such transmission may be made when the data is accumulated after a total amount of time, it may occur periodically, it may occur based on subject input at the client device, or it may occur based on a request signal received from the client device.

Figure 6:
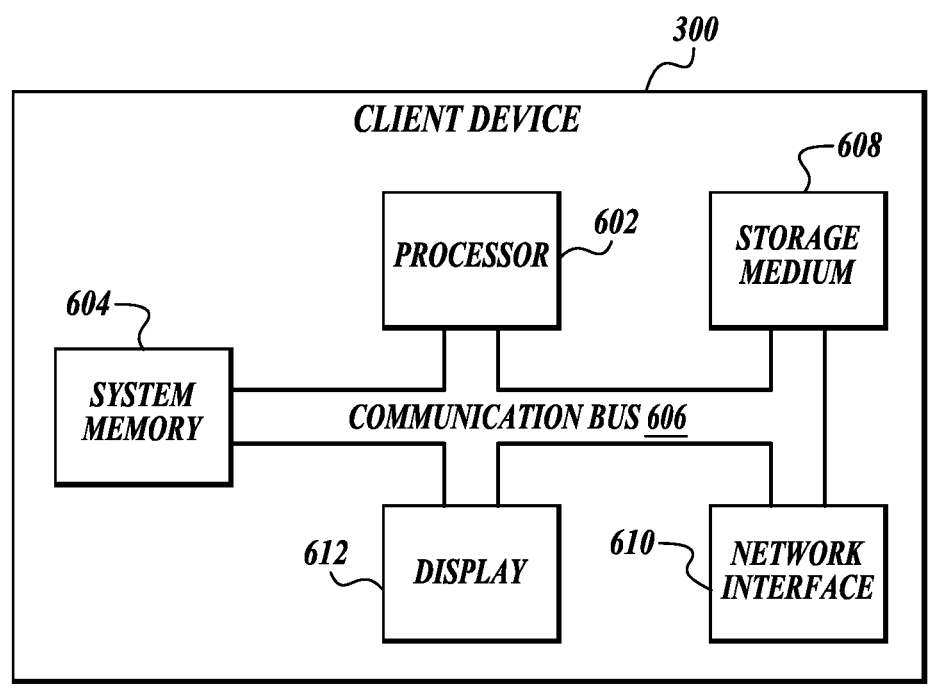
FIG. 6 is a diagrammatical illustration of components of a representative client device.

FIG. 6 is a block diagram that illustrates aspects of an exemplary client device 300. The description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the client device 300 may be any one of any number of currently available or yet to be developed devices.

In its most basic configuration, the client device 300 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the client device 300 by supporting the execution of instructions. In one embodiment, the processor 602 is configured to process the data from the UV sensor 100 into information that can be displayed on the display device 612. In one embodiment, the client device 300 transfers the data from the UV sensor 100 to a cloud server 302 or servers 304, which process the data from the UV sensor 100 into information that can then be transferred back to the client device 300 for display on the display device 612.

As further illustrated in FIG. 6, the client device 300 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 610 illustrated in FIG. 6 may represent one or more wireless interfaces or physical communication interfaces described and illustrated above with respect to particular components of the client device 300.

In the exemplary embodiment depicted in FIG. 6, the client device 300 also includes a storage medium 608. However, services may be accessed using a client device that does not include means for persisting data to a local storage medium. Therefore, the storage medium 608 depicted in FIG. 6 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 604 and storage medium 608 depicted in FIG. 6 are merely examples of computer-readable media.

Suitable implementations of client devices 300 that include a processor 602, system memory 604, communication bus 606, storage medium 608, network interface 610, and display 612 are known and commercially available. FIG. 6 does not show some of the typical components of many client devices. In this regard, the client device 300 may include input devices, such as a keyboard, keypad, mouse, microphone, touch input device, touch screen, tablet, and/or the like. Such input devices may be coupled to the client device 300 by wired or wireless connections including RF, infrared, serial, parallel, Bluetooth, Bluetooth low energy, USB, or other suitable connections protocols using wireless or physical connections. Similarly, the client device 300 may also include output devices such as a display, speakers, printer, etc.

In one embodiment, the display device 612 of the client device 300 is an LED display, an OLED display, or another type of display for presenting a user interface. In one embodiment, the display device may be combined with or include a touch-sensitive layer, such that a subject 102 may interact with a user interface presented on the display device 612 by touching the display. In one embodiment, a separate user interface device, including but not limited to a mouse, a keyboard, or a stylus, may be used to interact with a user interface presented on the display device.

Figure 7:
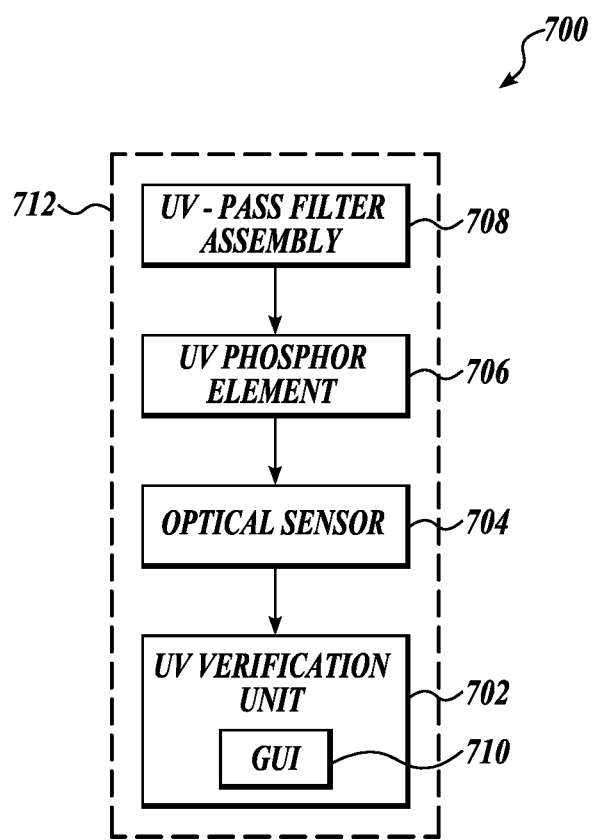
FIG. 7 is a diagrammatical illustration of a wearable UV sensor.

In FIG. 7, a wearable sensor 700 similar to sensor 100 is illustrated. The wearable sensor 700 comprises an ultraviolet verification unit 702 coupled to one or more optical sensors 704 and an ultraviolet phosphor element 706 configured to fluoresce in the visible light spectrum responsive upon receiving an interrogation by an ultraviolet stimulus, wherein the wearable sensor 700 includes at least one ultraviolet pass filter assembly 708 configured to block the visible portion of an impinging optical radiation stimulus, pass the ultraviolet portion of the impinging optical radiation stimulus onto the ultraviolet phosphor element; and wherein the ultraviolet verification unit includes processing circuitry configured to generate one or more instances of an ultraviolet exposure level based on a portion of a detected fluorescent response of the ultraviolet phosphor element that ranges from 400 nanometers to 700 nanometers. In one embodiment, the ultraviolet verification unit may include one or more of a processor, system memory, storage medium, display, network interface, and communications bus similar to the client device 300 of FIG. 6. In one embodiment, the optical sensor 704 includes any sensor capable of detecting light in the visible spectrum as described above. In one embodiment, the phosphor element 706 includes one or more UV phosphor materials similar to the UV phosphor material 204 described above. In one embodiment, the ultraviolet pass filter assembly 708 includes similar filter materials as the UV-pass filter 206 described above. In one embodiment, the ultraviolet verification unit 702 can be provided within or inside the same housing 712 as the optical sensor 704, ultraviolet phosphor element 706 and the ultraviolet pass filter assembly 708. In one embodiment, the ultraviolet verification unit 702 can be outside of the housing 712 and connected directly to the optical sensor 704, ultraviolet phosphor element 706 and the ultraviolet pass filter assembly 708.

In one embodiment, the ultraviolet verification unit 702 includes a graphical user interface 710 configured to generate the one or more instances of the ultraviolet exposure level based on the portion of a detected fluorescence response of the ultraviolet phosphor element that ranges from 400 nanometers to 700 nanometers.

In one embodiment, the ultraviolet verification unit 702 includes a graphical user interface 710 configured to generate the one or more instances of the ultraviolet exposure duration, an ultraviolet exposure intensity, an ultraviolet exposure severity, and a user-specific lifetime ultraviolet exposure status based on the portion of a detected fluorescent response of the ultraviolet phosphor element that ranges from 400 nanometers to 700 nanometers.

Representative embodiments may include, but, are not limited to the following.

In one embodiment, a UV sensor 100 comprises a UV pass filter 206; a UV phosphor material 204; and a visible light sensing device 202, wherein the UV sensor is configured to receive light including visible light and UV light, wherein the UV pass filter directs the UV light to the UV phosphor material and the UV phosphor material fluoresces visible light in proportion to the UV light from the UV pass filter, and the visible light sensing device measures the visible light fluorescing from the UV phosphor material to determine an amount of the UV light entering the UV sensor.

In one embodiment, the UV pass filter transmits the UV light and blocks the visible light and infrared light.

In one embodiment, the UV sensor comprises circuitry 202 to wirelessly transfer data to a client device 300.

In one embodiment, the UV sensor comprises a memory 202 configured to store data generated by the visible light sensing device.

In one embodiment, the UV sensor comprises a photodiode 214 to measure the visible light fluorescence.

In one embodiment, a combination of the UV sensor 100 and a client device 300 is described, wherein the UV sensor is configured to communicate data to the client device.

In one embodiment, the client device is a smart phone.

In one embodiment, the client device is configured to display the UV intensity.

In one embodiment, the client device is configured to display a cumulative UV exposure.

In one embodiment, the client device is configured to process the data from the UV sensor on a client device processor 602.

In one embodiment, the client device is configured to transfer the data from the UV sensor to a server 304 for processing the data.

In one embodiment, a method of measuring UV exposure of a subject 102 comprises wearing a UV sensor 100 by a subject 102; filtering 206 UV light entering the UV sensor from visible light entering the UV sensor; causing fluorescence 204 of visible light from the filtered UV light that is in proportion to the filtered UV light; measuring 202 the fluorescent visible light; and calculating UV light entering the sensor from the amount of fluorescent visible light to obtain an estimate of UV exposure of a subject 102.

In one embodiment, the method further comprises transferring data 406 from the UV sensor to a client device 300, wherein the client device calculates the amount of UV light entering the sensor.

In one embodiment, the client device displays the UV exposure of the subject 102 on a display device 612 of the client device.

In one embodiment, a wearable sensor 700 comprises an ultraviolet verification unit 702 coupled to one or more optical sensors 704 and an ultraviolet phosphor element 706 configured to fluoresce in the visible light spectrum responsive to an interrogation by an ultraviolet stimulus, wherein the wearable sensor includes at least one ultraviolet pass filter assembly 708 configured to block the visible portion of an impinging optical radiation stimulus, pass the ultraviolet portion of the impinging optical radiation stimulus onto the ultraviolet phosphor element; and wherein the ultraviolet verification unit includes processing circuitry configured to generate one or more instances of an ultraviolet exposure level based on a portion of a detected fluorescent response of the ultraviolet phosphor element that ranges from 400 nanometers to 700 nanometers.

In one embodiment, the ultraviolet verification unit 702 includes a graphical user interface 710 configured to generate the one or more instances of the ultraviolet exposure level based on the portion of a detected fluorescent response of the ultraviolet phosphor element that ranges from 400 nanometers to 700 nanometers.

In one embodiment, the ultraviolet verification unit 702 includes a graphical user interface 710 configured to generate the one or more instances of the ultraviolet exposure duration, an ultraviolet exposure intensity, an ultraviolet exposure severity, and a user-specific lifetime ultraviolet exposure status based on the portion of a detected fluorescent response of the ultraviolet phosphor element that ranges from 400 nanometers to 700 nanometers.

While illustrative embodiments have been illustrated and described, it will be appreciated that various changes can be made therein without departing from the spirit and scope of the invention.

The embodiments of the invention in which an exclusive property or privilege is claimed are defined as follows:

1. A UV sensor, comprising:
    a lens that allows light including visible and UV light to enter the UV sensor;
    after the lens, a UV pass filter directs the UV light to a UV phosphor material;
    after the UV pass filter, the UV phosphor material fluoresces visible light in proportion to the UV light from the UV pass filter; and
    after the UV phosphor material, a visible light sensing device measures the visible light fluorescing from the UV phosphor material to determine an amount of the UV light entering the UV sensor.

2. The UV sensor of claim 1, wherein the UV pass filter transmits the UV light and blocks the visible light and infrared light.

3. The UV sensor of claim 1, comprising circuitry to wirelessly transfer data to a client device.

4. The UV sensor of claim 1, comprising a memory configured to store data generated by the visible light sensing device.

5. The UV sensor of claim 1, comprising a photodiode to measure the visible light fluorescence.

6. A combination, comprising:
    the UV sensor of claim 1; and
    a client device, wherein the UV sensor is configured to communicate data to the client device.

7. The combination of claim 6, wherein the client device is a smart phone.

8. The combination of claim 6, wherein the client device is configured to display the UV intensity.

9. The combination of claim 6, wherein the client device is configured to display a cumulative UV exposure.

10. The combination of claim 6, wherein the client device is configured to process the data from the UV sensor on a client device processor.

11. The combination of claim 6, wherein the client device is configured to transfer the data from the UV sensor to a server for processing the data.

12. A method of measuring UV exposure of a subject, comprising:
    wearing a UV sensor of claim 1 by a subject;
    filtering UV light entering the UV sensor from visible light entering the UV sensor;
    causing fluorescence of visible light from the filtered UV light that is in proportion to the filtered UV light;
    measuring the fluorescent visible light; and
    calculating UV light entering the sensor from the amount of fluorescent visible light to obtain an estimate of UV exposure of a subject.

13. The method of claim 12, further comprising transferring data from the UV sensor to a client device, wherein the client device calculates the amount of UV light entering the sensor.

14. The method of claim 13, wherein the client device displays the UV exposure of the subject on a display device of the client device.

15. A wearable sensor, comprising: the UV sensor of claim 1 and an ultraviolet verification unit coupled to the UV sensor, wherein the ultraviolet verification unit includes processing circuitry configured to generate one or more instances of an ultraviolet exposure level based on a portion of a detected fluorescent response of the UV phosphor material that ranges from 400 nanometers to 700 nanometers.

16. The wearable sensor of claim 15, wherein the ultraviolet verification unit includes a graphical user interface configured to generate the one or more instances of the ultraviolet exposure level based on the portion of a detected fluorescent response of the UV phosphor material that ranges from 400 nanometers to 700 nanometers.

17. The wearable sensor of claim 15, wherein the ultraviolet verification unit includes a graphical user interface configured to generate the one or more instances of the ultraviolet exposure duration, an ultraviolet exposure intensity, an ultraviolet exposure severity, and a user-specific lifetime ultraviolet exposure status based on the portion of a detected fluorescent response of the UV phosphor material that ranges from 400 nanometers to 700 nanometers.

* * * * *